(12) United States Patent
Fujioka et al.

(10) Patent No.: US 11,147,248 B2
(45) Date of Patent: Oct. 19, 2021

(54) METHOD FOR PRODUCING ACOUSTIC TRAUMA DEAFNESS MODEL ANIMAL, AND ACOUSTIC TRAUMA DEAFNESS MODEL ANIMAL PRODUCED BY THE SAME

(71) Applicants: KEIO UNIVERSITY, Tokyo (JP); THE JIKEI UNIVERSITY SCHOOL OF MEDICINE, Tokyo (JP)

(72) Inventors: Masato Fujioka, Tokyo (JP); Hirotaka James Okano, Tokyo (JP); Hiromi Kojima, Tokyo (JP); Sho Kurihara, Tokyo (JP); Tomohiko Yoshida, Tokyo (JP)

(73) Assignees: KEIO UNIVERSITY, Tokyo (JP); THE JIKEI UNIVERSITY SCHOOL OF MEDICINE, Tokyo (JP)

( * ) Notice: Subject to any disclaimer, the term of this patent is extended or adjusted under 35 U.S.C. 154(b) by 142 days.

(21) Appl. No.: 16/197,742

(22) Filed: Nov. 21, 2018

(65) Prior Publication Data

US 2019/0174728 A1    Jun. 13, 2019

(30) Foreign Application Priority Data

Sep. 21, 2017    (JP) .............................. JP2017-181683

(51) Int. Cl.
    *A01K 67/027*    (2006.01)
(52) U.S. Cl.
    CPC ........ *A01K 67/027* (2013.01); *A01K 2207/35* (2013.01); *A01K 2227/106* (2013.01); *A01K 2267/03* (2013.01)
(58) Field of Classification Search
    CPC .............. A01K 67/027; A01K 2207/35; A01K 2227/106; A01K 2267/03
    See application file for complete search history.

(56) References Cited

U.S. PATENT DOCUMENTS

| 2002/0004516 A1 | 1/2002 | Stutzmann et al. |
| 2008/0275034 A1 | 11/2008 | Pignol et al. |
| 2017/0333403 A1 | 11/2017 | Hosoya et al. |

FOREIGN PATENT DOCUMENTS

| JP | 2002-532424 A | 10/2002 |
| JP | 2007-530640 A | 11/2007 |
| JP | 2009-544712 A | 12/2009 |
| JP | 2011-037738 A | 2/2011 |
| JP | 2011-219497 A | 11/2011 |
| JP | 2015-172071 A | 10/2015 |
| WO | WO 2008/013866 | 1/2008 |
| WO | WO-2011/028503 A1 | 3/2011 |
| WO | WO-2016/117431 A1 | 7/2016 |

OTHER PUBLICATIONS

Pugh et al., Arch. Otorhinolaryngol. 224, 241-255, 1979.*
Valero et al. Hearing Research 353 (2017) 213e223, published online Jul. 8, 2017.*
Hosoya et al., Scientific Reports; 6:22250, pp. 1-12, 2016.*
Fujioka et al., "Proinflammatory Cytokines Expression in Noise-Induced Damaged Cochlea," *Journal of Neuroscience Research* 83:575-583 (2006).
Hosoya et al., "Distinct Expression Pattern of a Deagness Gene, KIAA1199, in a Primate Cochlea," *BioMed Research International*, vol. 2016, Article ID 1781894.
Sato et al., "Time Course of Changes in CAP and DPOAE in Guinea Pig Loaded with Loud Sound," *Audiology Japan*, 39(5), pp. 553-554 (1996).
Hunter-Duvar et al., "Effects of intense auditory stimulation: hearing losses and inner ear changes in the squirrel monkey," *The Journal of the Acoustical Society of America*, vol. 54, p. 1179-p. 1183 (1973).

* cited by examiner

*Primary Examiner* — Thaian N. Ton
(74) *Attorney, Agent, or Firm* — Marshall, Gerstein & Borun LLP

(57) ABSTRACT

A method for producing a new deafness model animal and a new deafness model animal produced by the method, enabling research that can also be applied to clinical application to a human. The present invention provides a method for producing an acoustic trauma deafness model animal, the method including exposing a non-human primate animal to a sound having a frequency of 1 kHz to 32 kHz and a sound pressure level of 100 dB to 150 dB for 10 minutes to 360 minutes. In addition, the present invention provides an acoustic trauma deafness model animal provided by the method for producing an acoustic trauma deafness model animal.

7 Claims, 9 Drawing Sheets

APICAL TURN (LESS THAN 1 kHz)

CONTROL
myo7a

AFTER EXPOSURE TO SOUND

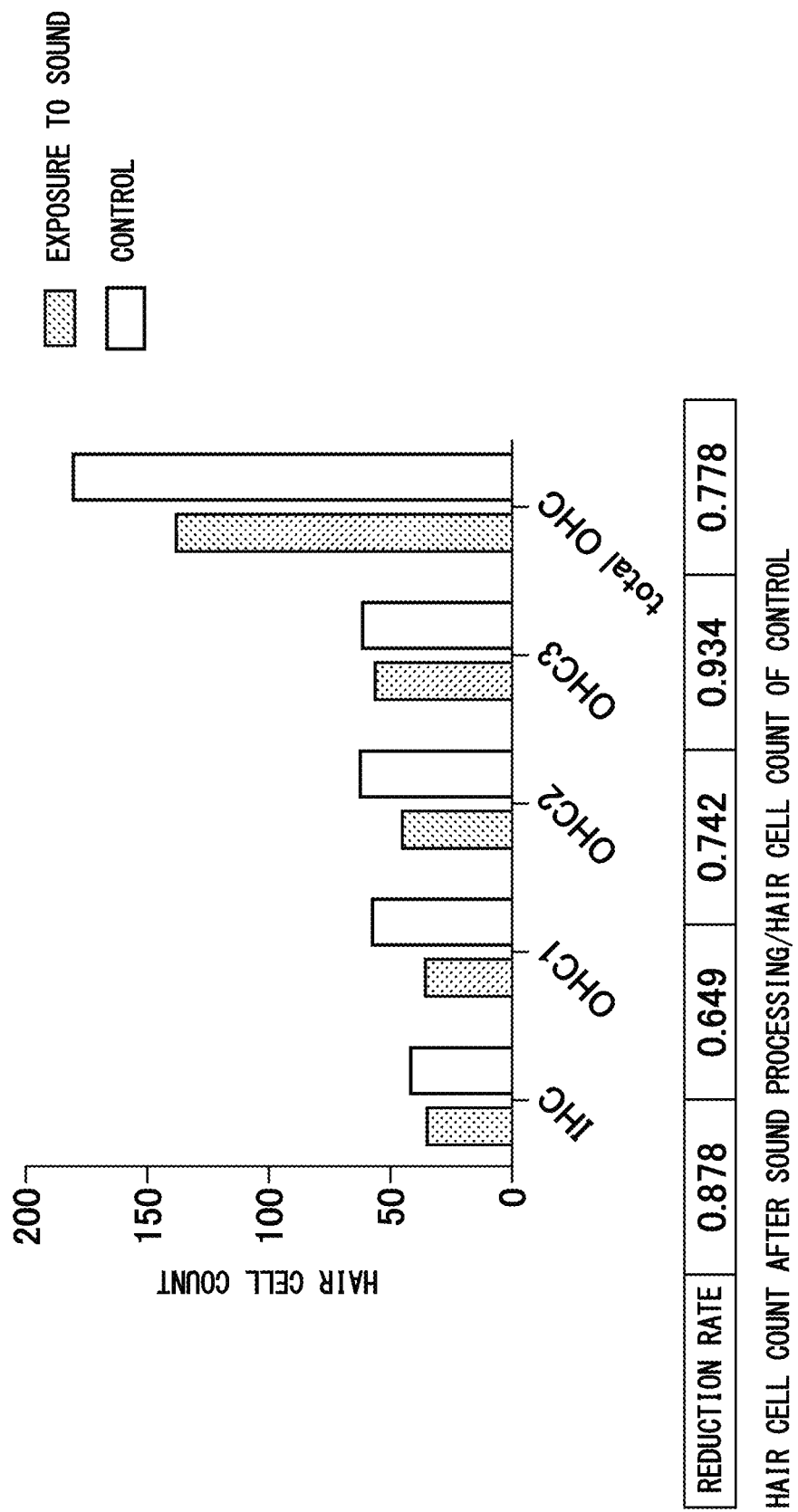

MIDDLE TURN (ABOUT 1 kHz)

CONTROL

AFTER EXPOSURE TO SOUND

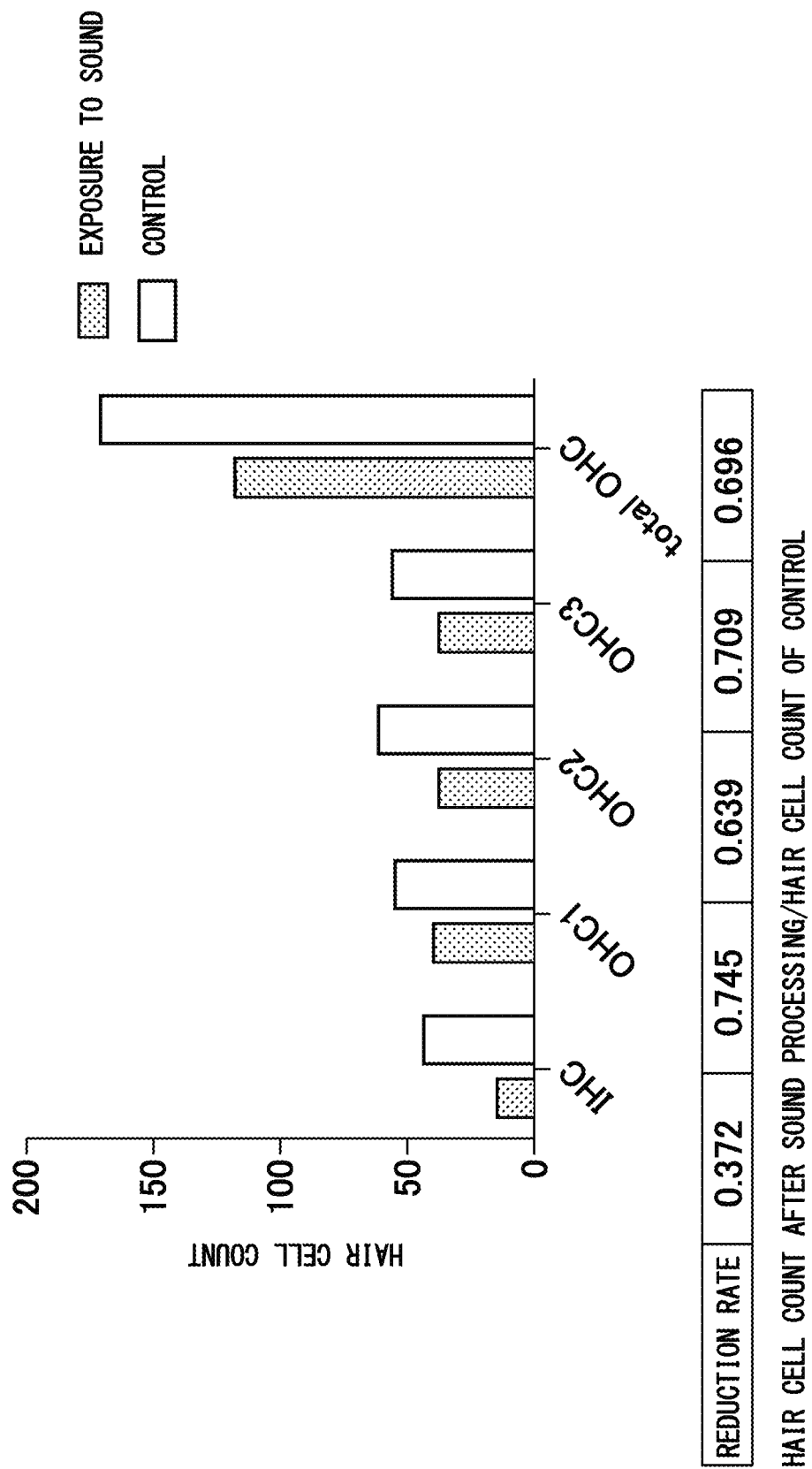

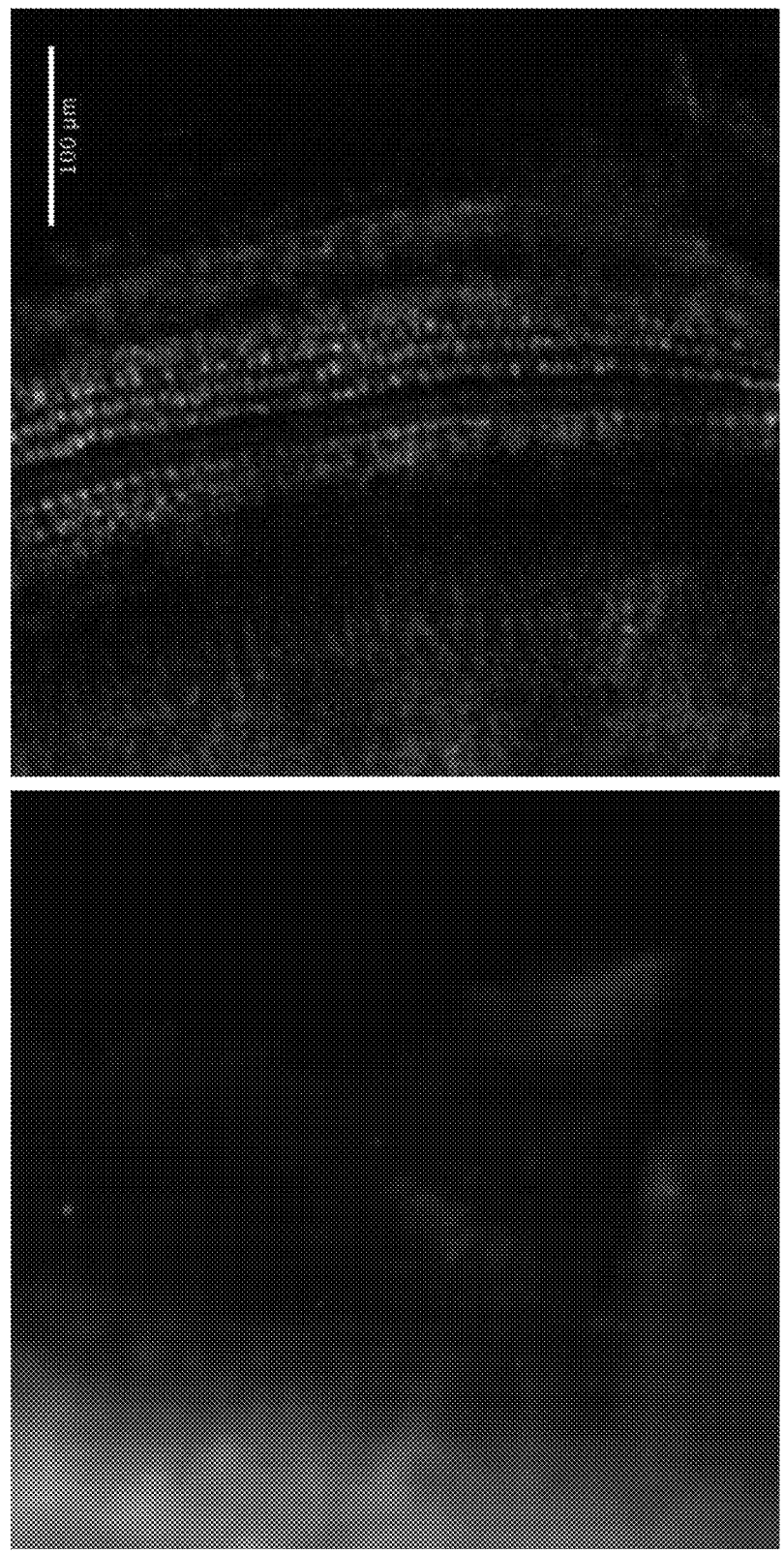

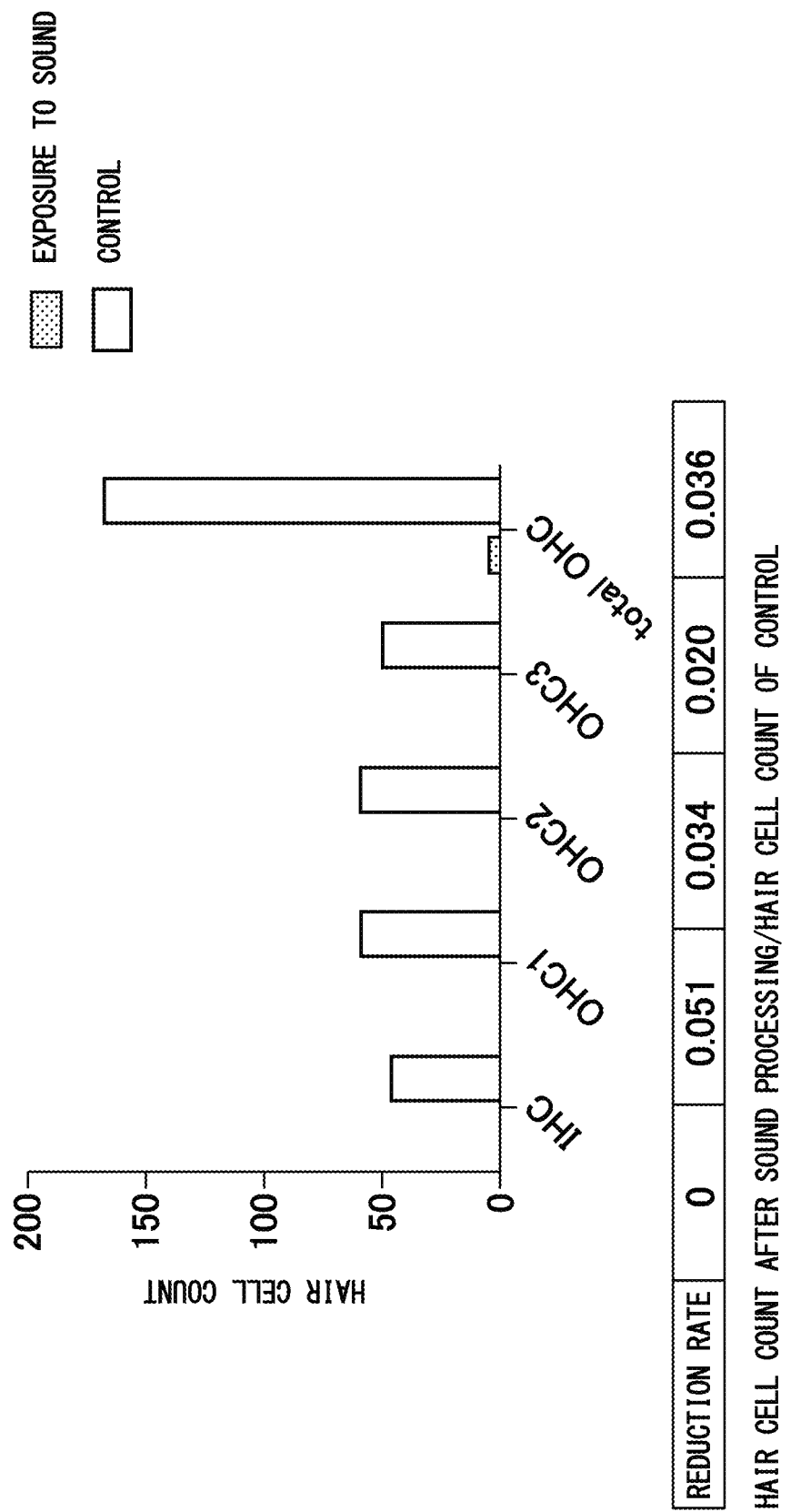

METHOD FOR PRODUCING ACOUSTIC TRAUMA DEAFNESS MODEL ANIMAL, AND ACOUSTIC TRAUMA DEAFNESS MODEL ANIMAL PRODUCED BY THE SAME

TECHNOLOGICAL FIELD

The present invention relates to a method for producing an acoustic trauma deafness model animal. Moreover, the present invention relates to an acoustic trauma deafness model animal produced by the method.

BACKGROUND

The auditory sense, which is one of so-called five senses, refers to the function of converting sonic waves in a certain range into an electric signal through the external, middle, and inner ears to recognize the electric signal by the auditory cortex through the auditory nerve. Information based on sounds can be perceived by the auditory sense, and therefore, the auditory sense in indispensable sense for communication.

A state in which the auditory sense is deteriorated is called deafness and seriously affects daily life depending on the degree of deafness. In recent years, the number of patients with deafness has tended to increase due to noises from factories and the like, the proliferation of portable music players, and the like. In Japan, which has headed into a super-aging society, the number of patients with deafness developed due to ageing has increased steadily. Therefore, the development of a method capable of treating and preventing deafness is urgent.

Deafness model animals have been developed in order to research the causes of deafness and to develop new treatment methods. Such research is currently being carried out on deafness model animals including mice as well as rats, guinea pigs, cats, dogs, and rabbits (for example, Japanese Unexamined Patent Publication (Kokai) No. 2011-37738 and Shigenori Sato, et al., "Time Course of Changes in CAP and DPOAE in Guinea Pig Loaded with Loud Sound", Audiology Japan, 39 (5), pp. 553-554, September, 1996).

There are many differences between humans and deafness model animals used in conventional research in the form and development mechanism of the inner ear. The humans and the deafness model animals also greatly differ in the expression system for communication with other individuals. Therefore, the clinical application of findings obtained from conventional deafness model animals to humans on an as-is basis has been problematic.

In methods for producing conventional deafness model animals, particularly acoustic trauma deafness model animals, the amounts of loads with sound pressures have been sometimes insufficient, and the hearing levels of the animals obtained thereby have varied. Such problems have inhibited function experiments for developing treatment methods.

Therefore, it is an object of the present invention to provide a method for producing a new deafness model animal and a new deafness model animal produced by the method, enabling research that can also be applied to clinical application to a human.

SUMMARY

The present inventors have conducted research and development by performing examination from various angles in order to solve the problems described above. As a result, it was surprisingly found that an acoustic trauma deafness model animal can be reproducibly produced by exposing a non-human primate animal to a sound under certain conditions. In other words, the present invention is as follows.

[1] A method for producing an acoustic trauma deafness model animal, the method including exposing a non-human primate animal to a sound having a frequency of 1 kHz to 32 kHz and a sound pressure level of 100 dB to 150 dB for 10 minutes to 360 minutes.

[2] The method according to [1], wherein the frequency has an octave band of which a center is any frequency of 1 kHz to 32 kHz.

[3] The method according to [1] or [2], wherein the frequency has an octave band of which a center is any frequency of 4 kHz to 16 kHz.

[4] The method according to any one of [1] to [3], wherein the sound pressure level is 125 dB to 150 dB.

[5] The method according to any one of [1] to [4], wherein both ears are exposed to the sound from outsides of external ears of the non-human primate animal, respectively.

[6] The method according to any one of [1] to [5], the method being performed under intubation management with an artificial respirator under general anesthesia.

[7] The method according to any one of [1] to [6], wherein the non-human primate animal is a New World monkey.

[8] The method according to any one of [1] to [7], wherein the non-human primate animal is a common marmoset.

[9] A non-human primate animal produced by the method according to any one of [1] to [8].

[10] The non-human primate animal according to [9], wherein the non-human primate animal is a common marmoset.

The present invention enables reproducible provision of a new deafness model animal enabling research that can also be applied to clinical application to a human.

BRIEF DESCRIPTION OF DRAWINGS

(FIG. 2A) before exposure to a sound; and (FIG. 2B) after exposure to the sound.

(FIG. 3A) before exposure to a sound (4 kHz); (FIG. 3B) after exposure to the sound (4 kHz); (FIG. 3C) before exposure to a sound (16 kHz); and (FIG. 3D) after exposure to the sound (16 kHz). DPOAE is objective audiometry that reflects the acoustic wave amplification ability of cochlear outer hair cells, and the functional decline of the outer hair cells also results in a decrease in DPOAE level (sound pressure). A DPOAE level is known to be also decreased in a nonlinear regression manner with a decrease in stimulus sound pressure. The ordinate represents the sound pressure of the DPOAE level of a common marmoset while the abscissa represents a stimulus sound pressure. The higher sound pressure of the DPOAE level represents the more favorable function of outer hair cells. Noise Floor indicates the total sum of noise produced by a measurement instrument in itself, noise added from an ambient environment, and any noise produced from a measurement individual in itself.

FIG. 4C illustrates a graph of the counts of the hair cells FIG. 4A and FIG. 4B. IHC: inner hair cells, OHC 1 to 3: outer hair cells 1 to 3 (the numerical characters denote column numbers).

FIG. 5C illustrates a graph of the counts of the hair cells FIG. 5A and FIG. 5B. IHC: inner hair cells, OHC 1 to 3: outer hair cells 1 to 3 (the numerical characters denote column numbers).

FIGS. 6A and 6B illustrate the state of the hair cells in the basal turn area of the cochlea of a common marmoset before and after performing the method of the present invention in one embodiment. A microphotograph illustrating the hair cells in the basal turn area of the cochlea (FIG. 6A) after exposure to a sound or (FIG. 6B) in a control is illustrated.

FIG. 6C illustrates a graph of the counts of the hair cells FIG. 6A and FIG. 6B. IHC: inner hair cells, OHC 1 to 3: outer hair cells 1 to 3 (the numerical characters denote column numbers).

DESCRIPTION OF EMBODIMENTS

Figure 1:
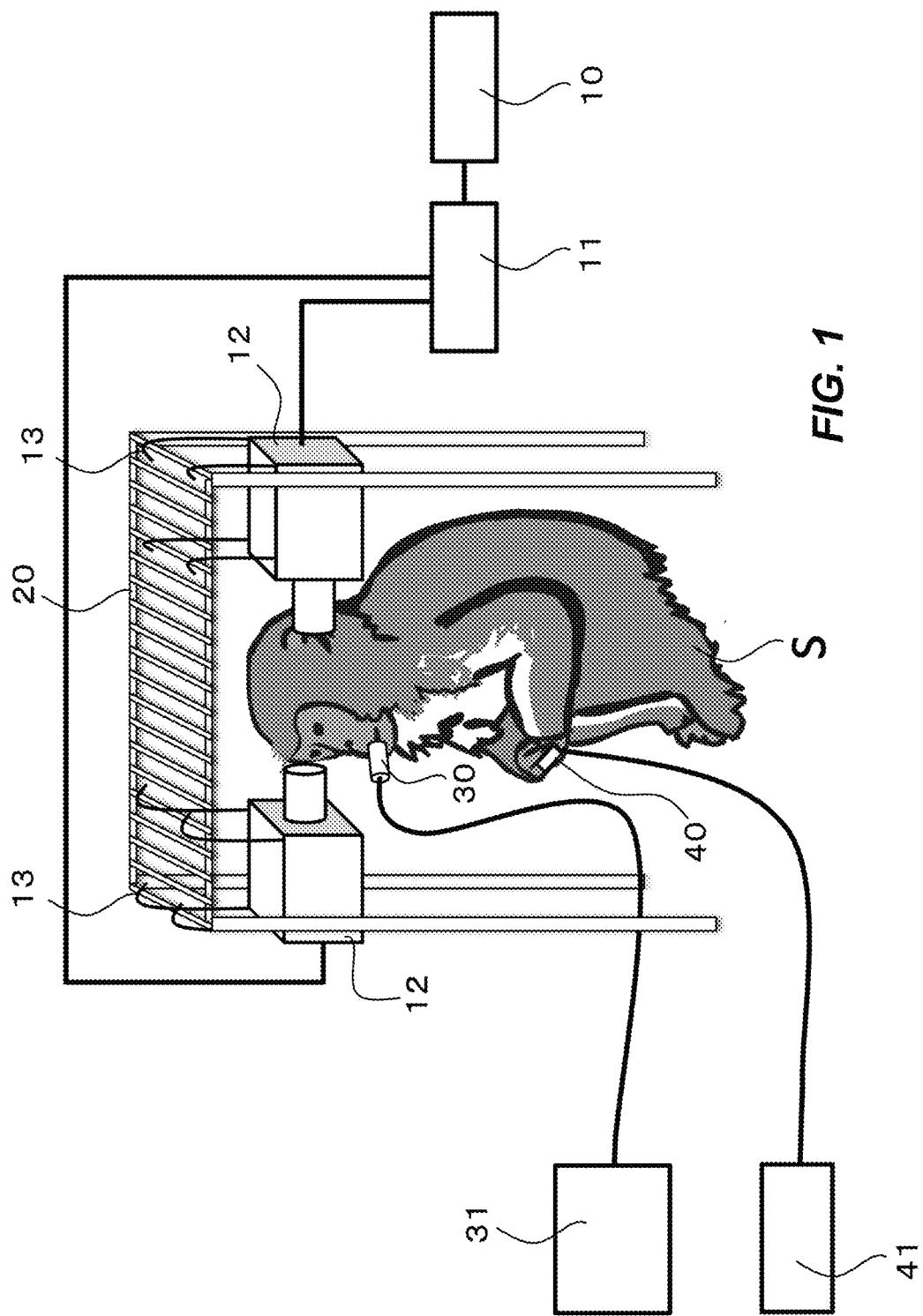
FIG. 1 is a schematic view illustrating a sound exposure apparatus that produces an acoustic trauma deafness model animal of the present invention in one embodiment.

Terms used herein are intended to describe a specific embodiment of the present invention and are not intended to limit the present invention. Unless particularly defined, all technological and scientific terms used herein mean the same as those commonly understood by those skilled in the art to which the present invention belongs.

Embodiments of the present invention will be described below with reference to the drawings if necessary. The configurations of the embodiments are illustrative, and the configuration of the present invention is not limited to the specific configurations of the embodiments.

<Acoustic Trauma Deafness Model Animal>

Herein, "acoustic trauma deafness model animal" refers to an animal of which the auditory sense is impaired by an acoustic load and is deteriorated in comparison with a conspecific animal to which the acoustic load is not applied.

Deafness is classified roughly into conduction deafness and sensorineural deafness. The conduction deafness refers to deafness caused by a change in transmission characteristics due to impairment of any or all of the external ear, the middle ear, the cochlear window, and the vestibular window. The sensorineural deafness refers to deafness in which any impairment of the inner ear or any site between the inner ear and the auditory center is considered to occur although the energy of a sound input from the external ear or the cranial bone is converted into the vibration of the inner ear lymph. One of the causes of the sensorineural deafness is acoustic trauma. Herein, acoustic trauma deafness refers to deafness caused by the impairment of the cochlea (for example, the hair cells of the cochlea) of the inner ear due to a strong sonic wave.

Commonly, acoustic trauma is caused by a sound with strong energy, such as lightning strike, explosion, a drop of a heavy product, mechanical chatter, a sound from a music instrument making a strong sound, such as a brass instrument, a sound from a music instrument or singing voice, electrically amplified by an amplifier, or music reproduced at megavolume. Acoustic trauma deafness includes deafness in which a hearing ability will be recovered and deafness in which a hearing ability will not be recovered. The method of the present invention provides an acoustic trauma deafness model animal of which the hearing ability will not be recovered in a certain period unless treatment and the like of the animal is particularly performed.

A conventional acoustic trauma deafness model animal has been produced by putting an awakened subject animal in a certain period in a box in which a speaker for presenting a sound pressure is placed (exposure to a sound under a free field). In this technique, a model animal can be easily produced if an apparatus is prepared once; however, a subject animal in itself may take on the behavior of protecting the ears from a sound, and as a result, the ears with the insufficient amount of sound pressure load may be often produced. This has caused the internal error of an acoustic trauma deafness model at a baseline and has often precluded a function experiment for developing a treatment method. A large difference between right and left hearing abilities in audiometry has caused a measurement error in shadow hearing and has precluded precise audiometry.

The present invention solves such problems as described above and is capable of reproducibly providing an acoustic trauma deafness model animal of which the hearing level is decreased to an optional level.

Herein, an acoustic trauma deafness model animal refers to a mammalian primate animal excluding a human (hereinafter referred to as "non-human primate animal"). In other words, the present invention provides an acoustic trauma deafness model animal including a non-human primate animal.

Primate animals include a group of so-called monkeys, including humans. Therefore, the primate animals and the humans have a lot in common and are therefore preferred as the acoustic trauma deafness model animal of the present invention. Primates are classified into strepsirrhines and haplorhines, and the latter are further classified into platyrrhines (New World monkeys) and catarrhines. The catarrhines are classified into a group of Old World monkeys including cercopithecoid and colobus, and a group of anthropoid apes and humans. The platyrrhines (New World monkeys) include marmosets and capuchins. The acoustic trauma deafness model animal of the present invention may be any of animals belonging to primates excluding humans, and is preferably a New World monkey, more preferably a marmoset, and most preferably a common marmoset.

A common marmoset (*Callithrix jacchus*) is a small monkey having a body length of less than 200 mm and a body weight of less than 300 g. The pregnancy period of a common marmoset is about five months. Typically, a common marmoset delivers dizygotic twins (up to three). A common marmoset becomes capable of copulating about ten days after delivery. A common marmoset can also deliver two times a year. A common marmoset becomes an adult around one and a half years after its birth. A common marmoset is used as an experimental animal because of being a primate animal which has excellent fecundity, and of which the analysis of the genome has also been completed. The ES and iPS cells of a common marmoset have also been established, and the production of a transgenic common marmoset has also succeeded.

Organs that control the auditory sense of a common marmoset are often anatomically similar to those of a human. In particular, the inner ear of a common marmoset is easily approached, and therefore, the common marmoset is a primate animal of which surgical treatment can be easily performed. A common marmoset has been found to have the central auditory pathway similar to that of a human. At present, a common marmoset is only an animal proved to have a neuron by which music is perceived.

A common marmoset is known to make a speech of a combination of a large number of characteristic voices in order to carry out communication with another individual. Examples of the kinds of the speeches of a common marmoset include "phee" which is a voice like a whistle, "trill" which is a vibrate-like low-tone voice, and "trillphee" and "twitter" which are combinations thereof. When being a common marmoset, the acoustic trauma deafness model animal of the present invention makes less speeches than a common marmoset with normal hearing. This is a phenomenon that is also observed in a human patient with deafness, and therefore, the acoustic trauma deafness model animal can be considered to be a model animal in which an influence caused by deafness on communication can also be observed.

<Method for Evaluating Deafness Level>

A known method can be used as a method for evaluating the degree of the deafness of the acoustic trauma deafness model animal. For example, the degree can be evaluated by examining auditory brain-stem response (ABR) or otoacoustic emission (OAE).

ABR is the potential of the brain stem, generated by exciting the auditory nervous system. The hearing ability of the subject can be determined by analyzing ABR (brain waves) generated by applying a certain sonic stimulation to the acoustic trauma deafness model animal. The abnormality of the auditory pathway (retrocochlear) primarily from the auditory nerve to the brain can be detected by measuring the ABR.

OAE refers to a sound from the hair cells in the inner ear, which is detected in the external auditory meatus. Examples of OAE include spontaneous otoacoustic emission (SOAE), evoked otoacoustic emission (EOAE), and distortion product otoacoustic emission (DPOAE). SOAE refers to an examination for detecting narrowband signals similar to a pure sound, voluntarily generated in the cochlea, by the spectrum analysis of the signals. EOAE is an examination for recording, as an acoustic signal, an acoustic emission evoked by a sound stimulus (click, tone burst, or the like) from the outside. DPOAE is an examination for detecting a sound as a distortion product other than two pure sounds having different frequencies, simultaneously applied to the external auditory meatus, and has a high frequency characteristic. Therefore, DPOAE is often used when audiometry at a specified frequency is performed. The deafness level of the acoustic trauma deafness model animal obtained by the present invention can be evaluated using any of the methods described above or a combination thereof.

<Method for Producing Acoustic Trauma Deafness Model Animal>

The method of the present invention enables reproducible provision of an acoustic trauma deafness model animal enabling research that can also be applied to clinical application to a human. The method of the present invention includes the following steps.

A method for producing an acoustic trauma deafness model animal, the method including exposing a non-human primate animal to a sound having a frequency of 1 kHz to 32 kHz and a sound pressure level of 100 dB to 150 dB for 10 minutes to 360 minutes.

The non-human primate animal used in the method of the present invention is an animal belonging to primates excluding humans. An acoustic trauma deafness model animal that is biologically and anatomically similar to a human can be provided by using the non-human primate animal. The acoustic trauma model animal can be reproducibly produced without variations in deafness level as in the case of a conventional deafness model animal.

The sound used in the method of the present invention is a sound having a frequency in a range of 1 kHz to 32 kHz. The sound used in the method of the present invention is a sound preferably having an octave band of which the center is any frequency of 1 kHz to 32 kHz, still more preferably having an octave band of which the center is any frequency of 4 kHz to 16 kHz, and for example, having an octave band of which the center is a frequency of 8 kHz. As a result, damage precluding recovery to a normal state when no treatment is performed can be efficiently caused in the inner ear. Herein, "n octave band" refers to a frequency width (band width) in which the rate between upper and lower limited frequencies of which the center is a certain frequency ($f_M$) is an n octave, and the upper and lower limited frequencies ($f_H$ and $f_L$) of the n octave band of which the center is a frequency (fm) are as follows.

$$\text{Lower limited frequency}(f_L) = f_H * 2\hat{\,}(-n/2) \qquad [\text{Math. 1}]$$

$$\text{Upper united frequency}(f_H) = f_M * 2\hat{\,}(n/2) \qquad [\text{Math. 2}]$$

Accordingly, for example, a sound having an octave band (1 octave band) of which the center is a frequency of 8 kHz means a sound having a frequency width of about 5.65 kHz to about 11.31 kHz.

Damage to a wide range of the hair cells of the cochlea (apical turn (less than 1 kH) to middle turn (about 1 kHz) to basal turn (about 16 kHz)), particularly the hair cells in the middle turn to basal turn of the cochlea, can be caused by loading a subject (acoustic trauma model animal) with a sound in a certain frequency width.

The sound used in the method of the present invention is a sound having a sound pressure level of 100 dB to 150 dB, and preferably a sound having a sound pressure level of 125 dB to 150 dB. The load with the sound having the sound pressure level enables the acoustic trauma model animal to be reproducibly produced without variations in deafness level as in the case of a conventional deafness model animal.

In one embodiment, the method of the present invention can be performed by a sound exposure apparatus 1 illustrated in FIG. 1. The sound exposure apparatus 1 includes: a sound generation apparatus 10 that generates a sound having a frequency of 1 kHz to 32 kHz; a sound amplification apparatus 11 that amplifies the sound generated by the sound generation apparatus 10 to a sound pressure level of 100 dB to 150 dB; and an external output apparatus 12 for outputting the sound amplified by the sound amplification apparatus 11. The external output apparatus 12 used in the method of the present invention may be a known speaker, may be a headphone-type external output apparatus which is worn so as to cover the whole ear, or may be an earphone-type external output apparatus which is inserted into the external acoustic meatus and worn. The sound generated in the method of the present invention results in generation of a large amount of heat because of being a sound having a sound pressure level of 100 dB to 150 dB and of having strong energy. Therefore, the external output apparatus 12 is preferably a speaker-type external output apparatus that enables exposure to a sound without bringing the apparatus into contact with an acoustic trauma deafness model animal S. The sound amplification apparatus 11 and the external output apparatus 12 may be integrated.

Although not illustrated in FIG. 1, the sound exposure apparatus 1 is put together with the acoustic trauma deafness model animal S in a sound-proof box.

In one embodiment, the sound exposure apparatus 1 used in the method of the present invention includes two external output apparatuses 12, and each of the external output apparatuses 12 is hung with a wiry arm 13 from a rack 20, and is used. One external output apparatus 12 may be used, or two or more external output apparatuses 12 are preferably used. When the two or more external output apparatuses 12 are used, the external output apparatuses 12 are preferably arranged at positions where both ears are exposed equally to a sound from the outsides of the external ears of the acoustic trauma deafness model animal S, as illustrated in FIG. 1. As a result, hypoacusis can be caused equally in the right and left ears. Since there are great species and individual differences in the position of the inlet of the external auditory meatus of the acoustic trauma deafness model animal S, the positions of the external output apparatuses 12 can be carefully adjusted by adjusting the lengths of the arms 13 and the positions at which the arms 13 are mounted on the rack 20. As a result, a sound pressure can be applied from the external output apparatuses 12 equally to both ears, and the acoustic trauma deafness model animal can be reproducibly produced. The external output apparatuses 12 may be enabled to be freestanding by using a stand or the like instead of hanging the external output apparatuses 12 from the rack 20. As a result, the external output apparatuses 12 can be freely arranged depending on the size and posture of the acoustic trauma deafness model animal S.

The method of the present invention is preferably performed under intubation management with the tracheal tube 30 of an artificial respirator 31, as illustrated in FIG. 1, under general anesthesia of the acoustic trauma deafness model animal S. The general anesthesia enables the acoustic trauma deafness model animal S to be safely fixed simultaneously with relieving the pain of the acoustic trauma deafness model animal S, and can cause the ears to be reliably exposed to a sound output from the external output apparatuses 12. The general anesthesia can be performed according to a known method. The acoustic trauma deafness model animal S may also be fixed by physically restraining the acoustic trauma deafness model animal S, instead of the general anesthesia.

The artificial respirator 31 is used to manage the respiration of the acoustic trauma deafness model animal S after performing the general anesthesia of the acoustic trauma deafness model animal S. For example, the oxygen saturation and heart rate of arterial blood are preferably monitored by a pulse oximeter 41 in order to monitor the general condition of the acoustic trauma deafness model animal S that is being exposed to a sound. An apparatus for detecting a rectal temperature, an apparatus for detecting the concentration of carbon dioxide in expired air, an apparatus for measuring the concentration of anesthesia in expired air, or the like may be further included in order to further monitor the general condition of the acoustic trauma deafness model animal S.

In the method of the present invention, the acoustic trauma deafness model animal S is exposed to the sound for 10 minutes to 360 minutes. The length of time for which the exposure to the sound is performed may be changed as appropriate depending on the magnitude of the sound pressure level, and is preferably 30 minutes to 300 minutes, more preferably 60 minutes to 240 minutes, and still more preferably 120 minutes to 240 minutes.

<Acoustic Trauma Deafness Model Animal Obtained by Method for Producing Acoustic Trauma Deafness Model Animal>

The acoustic trauma deafness model animal is provided by the method of the present invention. The provided acoustic trauma deafness model animal is an acoustic trauma deafness model animal of which the hearing ability is not recovered for a certain period of time and the deafness state is maintained unless treatment and the like of the animal is particularly performed, and which has almost no difference between right and left deafness levels. Therefore, a measurement error due to shadow hearing caused by a difference between right and left deafness levels, which has been problematic in a conventional acoustic trauma deafness model animal, is low, and precise audiometry is enabled.

EXAMPLES

The present invention will be described in more detail below with reference to an example. However, the present invention is not limited thereto at all. In the example, an experimental protocol using non-human primate animals was approved by the Ethical Review Board for animal experiment in the Jikei University School of Medicine and Keio University and was conducted according to "Fundamental Guidelines for Proper Conduct of Animal Experiment and Related Activities" (the Ministry of Education, Culture, Sports, Science and Technology).

1. Production of Acoustic Trauma Deafness Model Animal

Common marmosets (2 to 9 years old, Clea Japan, Inc.) with a normal hearing ability were used. Each individual into which 3 to 5% of isoflurane and triple-mixed intramuscular injection anesthesia (40 μg/kg of medetomidine, 0.4 mg/kg of midazolam, and 0.40 mg/kg of butorphanol) were introduced, and of which the intubation management with an artificial respirator was performed was put in a sound-proof box and allowed to be under a sound exposure apparatus. For exposure to a sound, a speaker (PDBT 35, manufactured by Pile Driver) was used, and each individual was exposed for 3 hours under two sound conditions of sound condition 1) 124 dB octave band of which the center was 8 kHz by the single speaker and sound condition 2) 130 dB octave band of which the center is 8 kHz by the two speakers. The heart rate, percutaneous blood oxygen saturation, rectal temperature, concentration of carbon dioxide in expired air, and concentration of isoflurane of each common marmoset which was being exposed to the sound were monitored. The following apparatus was used for the exposure to the sound.

<Sound Exposure Apparatus>

Speaker: PDBT 35, manufactured by Pile Driver

Rack (12 cm in height×20 cm in width×15 cm in depth)

Wire of 3 mm in diameter (for fixing the speaker to the rack and adjusting the position of the speaker)

Band noise generation apparatus: RION Audiometer AA-67N

Power amplifier: XLS 1502 (AMCRON (registered trademark))

2. Method for Evaluating Deafness Level

Figure 2A:
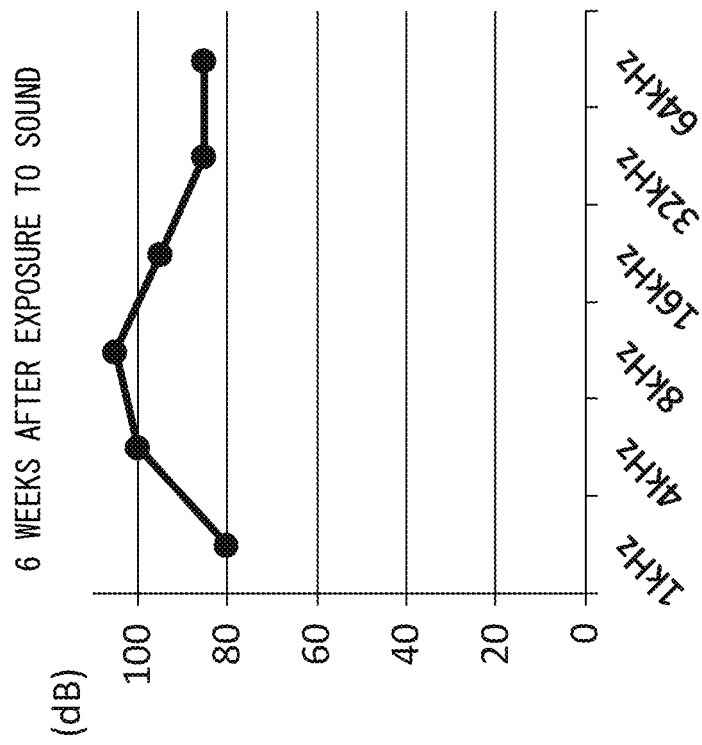
FIGS. 2A and 2B illustrate variations in the ABR threshold values of a common marmoset before and after performing a method of the present invention in one embodiment.
Figure 2B:
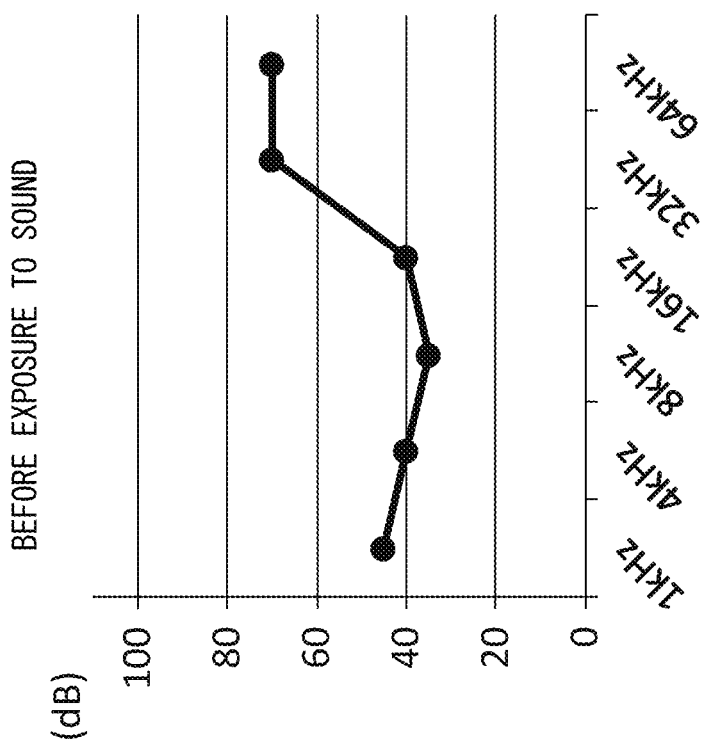
Figure 3A:
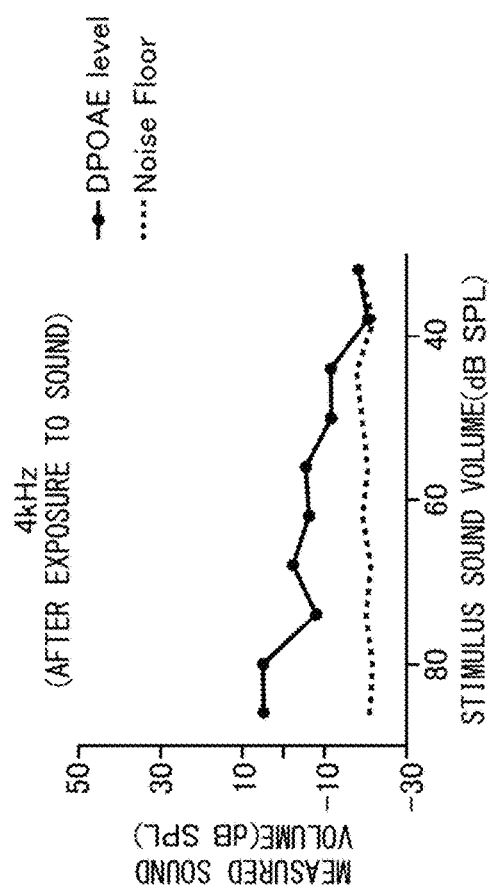
FIGS. 3A-3D illustrate variations in the DPOAE levels of a common marmoset before and after performing the method of the present invention in one embodiment.
Figure 3B:
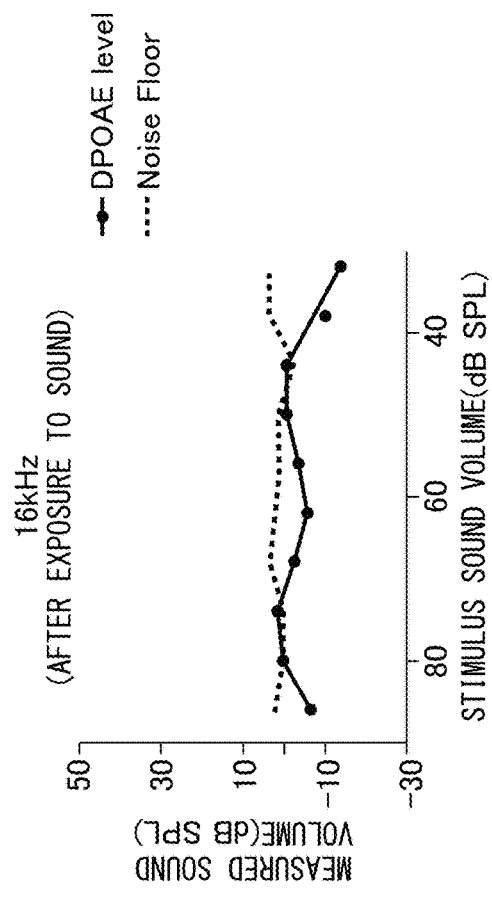
Figure 3C:
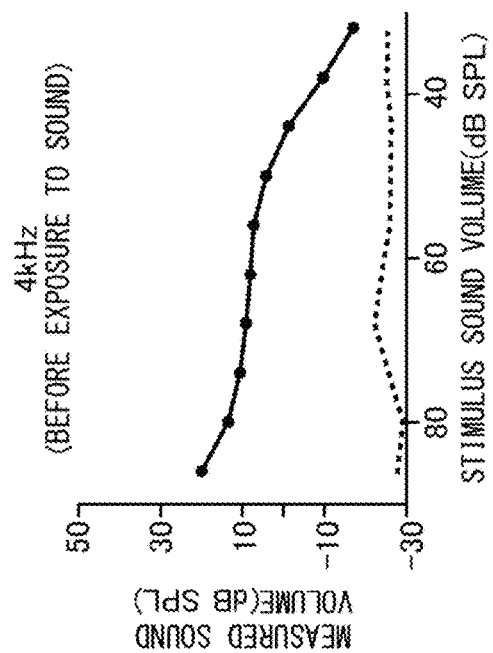
Figure 3D:
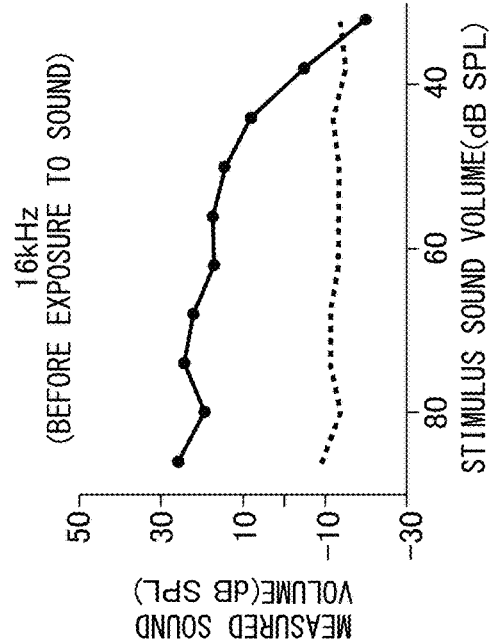
Figure 4B:
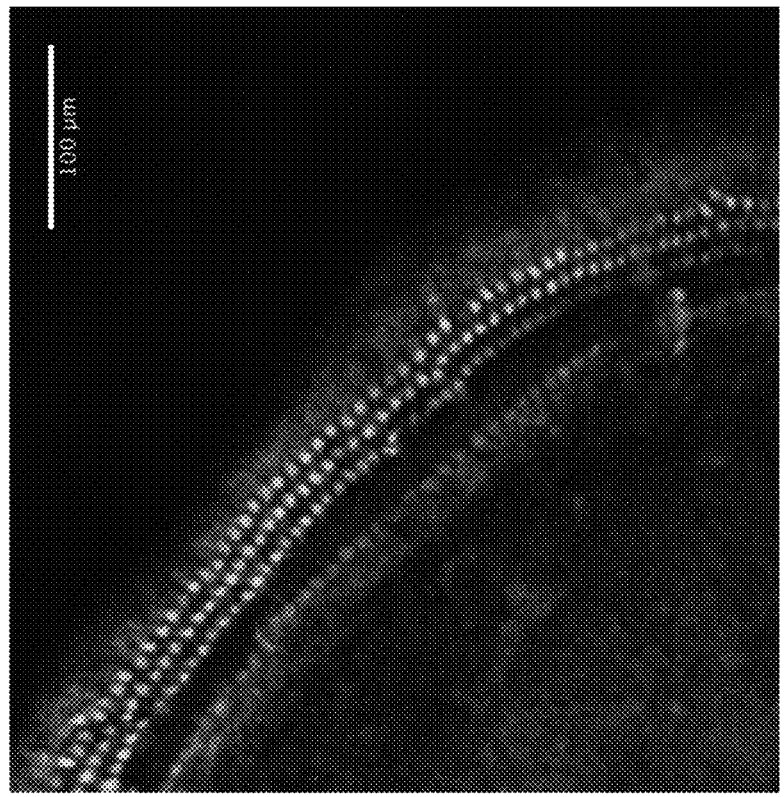
FIGS. 4A and 4B illustrate the state of the hair cells in the apical turn area of the cochlea of a common marmoset before and after performing the method of the present invention in one embodiment. A microphotograph illustrating the hair cells in the apical turn area of the cochlea (FIG. 4A) after exposure to a sound or (FIG. 4B) in a control is illustrated.
Figure 4A:
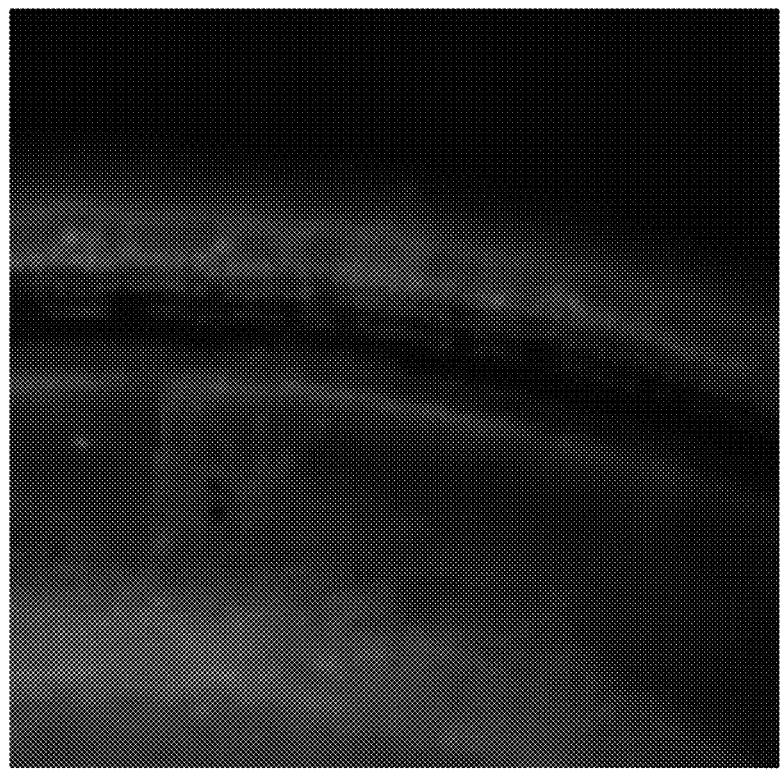
Figure 5B:
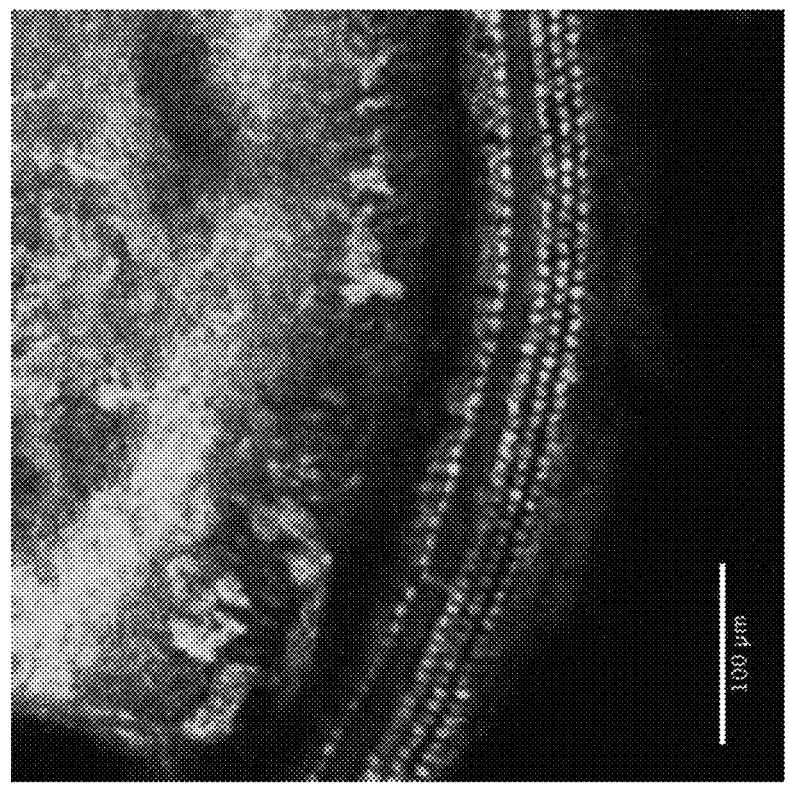
FIGS. 5A and 5B illustrate the state of the hair cells in the middle turn area of the cochlea of a common marmoset before and after performing the method of the present invention in one embodiment. A microphotograph illustrating the hair cells in the middle turn area of the cochlea (FIG. 5A) after exposure to a sound or (FIG. 5B) in a control is illustrated.
Figure 5A:
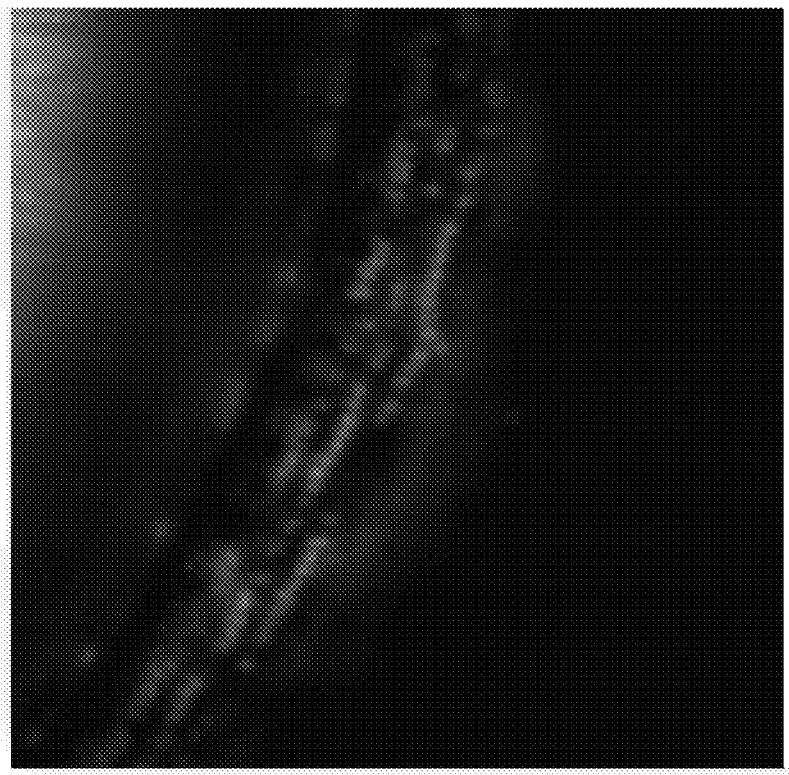

For the functional evaluation of acoustic trauma, ABR (FIGS. 2A and 2B) and DPOAE (FIGS. 3A-3D) before and after exposure to a sound were detected by the following instruments and procedure.

<ABR>
ABR measurement and sound generation apparatus (TDT (registered trademark) MF1, RP2.1, PAS, RA16)
Speaker (TDT (registered trademark) ED1), placed 1 cm apart from the tympanic membrane
Sonic stimulation: click: 0.1 msec pulses
tone burst: 1.0 msec duration
Analysis software: Waveforms obtained in BioSigRP were analyzed.
<DPOAE>
Measurement probe: ER-10C (Etymotic Research)
Digitization of measurement acoustic signal: RP2.1 (TDT (registered trademark))
Microphone Amplifier (produced by Bioresearch on consignment basis)
PC for acquiring and analyzing waveform: Dell Optilex 3020
Waveform analysis software, produced by Tatsuhiko Harada in International University of Health and Welfare, using LabView 3. Histological Analysis For histological evaluation, the Corti's organ was collected from each common marmoset exposed to the sound, and was immunostained using an anti-myo7a antibody, and the number of cochlear hair cells was quantified (FIGS. 4A-6C). The procedure will be specifically described below.

(1) Collection of specimen: The labyrinthine capsule including the cochlea was collected within 3 hours after euthanizing each common marmoset.

(2) Tissue Fixation: A 4% paraformaldehyde solution was injected from the round window and the oval window, and placement in the 4% paraformaldehyde solution in a 50 mL conical tube was performed at 4° C. for 2 days.

(3) Decalcification: The inner ear is covered with a bone tissue and therefore requires decalcification. The fixed sample was transferred to an EDTA (0.5 mM) solution and decalcified at room temperature for 3 weeks.

(4) Tissue collection: The decalcified capsule was removed, and the Corti's organ of the cochlea was collected.

(5) Immunostaining: Myo7a as a cochlear hair cell marker was immunostained using a mouse-produced anti-Myo7a antibody (Developmental Studies Hybridoma Bank, Antibody ID: AB_2282417) and a donkey-produced anti-mouse IgG antibody (Life Technologies, catalog number: A21202).

(6) Tissue observation: Observation and image capture were performed with a confocal microscope (ZEISS LSM880) after the immunostaining.

(7) Image analysis: The number of cells was counted using image analysis software ImageJ.

4. Behavioral Analysis

For behavioral analysis, the number and kinds of spoken words were recorded by picture recording and sound recording using the following instruments.

Sound recording and picture recording were simultaneously performed using:
Picture recording instrument: Handycam (registered trademark) HDR-CX390 (Sony Corporation, Japan); and
Sound recording instrument: Microphone AT9913 (Audio-Technica Corporation).

5. Results

Of two common marmosets loaded with the sound condition 1), one exhibited great variations in ABR threshold value and a permanent increase in threshold value while the other remained exhibiting a temporary increase in threshold value. In contrast, in the sound condition 2), a stable, permanent increase in threshold value in ABR, a decrease in DPOAE level, and an increase in threshold value were exhibited (FIGS. 2A-3D), and a reduction in cochlear hair cell (FIGS. 4A-6C) and a change and decrease in the number of spoken words were also confirmed (Table 1).

TABLE 1

|  | Exposure to sound | Normal hearing |
| --- | --- | --- |
| Phee | 3 | 28 |
| Trill | 3 | 4 |
| Trillphee | 0 | 2 |
| Twitter | 0 | 1 |
| Others | 2 | 5 |
| Total | 8 | 40 |

A common marmoset is closely similar to a human in view of temporal bone dissection, auditory physiological laboratory findings, and gene expression patterns. In the acoustic trauma models obtained in this case, deafness was confirmed to remain until 6 weeks after the exposure, and the models were considered to be permanent threshold value increase models. Common marmosets form a colony under a breeding environment and vigorously make language communication. The confirmation of decreases in the number and kinds of spoken words due to the exposure to the sound exhibited that this model may simulate the limitation of social activity associated with deafness. New research can be expected in future by melding the model with primate brain science such as fMRI or NIRS.

The stable common marmoset acoustic trauma model which has permanently increased threshold value, was established. Application is expected as a tool for acquiring non-clinical Proof Of Concept in translational research.

The invention claimed is:

1. A method for producing an acoustic trauma deafness model animal, the method comprising exposing a non-human primate animal to a sound having a frequency of 1 kHz to 32 kHz and a sound pressure level of 130 dB to 150 dB for 180 minutes to 360 minutes, the method being performed under general anesthesia,
wherein the frequency has an octave band of which a center is a frequency of 8 kHz,
wherein both ears are exposed to the sound from outsides of external ears of the non-human primate animal,
wherein the non-human primate animal is a common marmoset, and
wherein the acoustic trauma deafness model animal maintains an increase in threshold value of auditory brainstem response (ABR) generated by applying a sonic stimulation having a frequency of 1 kHz or more, for at least 6 weeks, compared to that of a normal hearing common marmoset.

2. The method according to claim 1, the method being performed under intubation management with an artificial respirator.

3. The method according to claim 1, wherein the acoustic trauma deafness model animal maintains a decrease in the number of spoken words, compared to that of the normal hearing common marmoset.

4. The method according to claim 1, wherein the number of hair cells in the middle turn to basal turn of cochlea of the acoustic trauma deafness model animal is less than that of the normal hearing common marmoset.

5. The method according to claim 1, wherein the sound pressure level is 130 dB.

6. The method according to claim 5, wherein the non-human primate animal is exposed to the sound for 180 minutes.

7. The method according to claim 1, wherein the non-human primate animal is exposed to the sound for 180 minutes.

\* \* \* \* \*